United States Patent [19]

Godel et al.

[11] Patent Number: 5,698,565

[45] Date of Patent: Dec. 16, 1997

[54] USE OF PHENOXY-PYRIDINE DERIVATIVES

[75] Inventors: Thierry Godel; Deborah Hartman, both of Basel, Switzerland; Claus Riemer, Schliengen, Germany

[73] Assignee: Hoffmann-La Roche Inc., Nutley, N.J.

[21] Appl. No.: 639,386

[22] Filed: Apr. 29, 1996

[30] Foreign Application Priority Data

Jun. 9, 1995 [CH] Switzerland .................. 1704/95

[51] Int. Cl.$^6$ .................................................. A61K 31/44
[52] U.S. Cl. .................................... 514/277; 514/357
[58] Field of Search ............................. 514/277, 357

[56] References Cited

U.S. PATENT DOCUMENTS

| | | | |
|---|---|---|---|
| 3,528,976 | 9/1970 | Budnowski et al. | 514/277 |
| 3,723,445 | 3/1973 | Edonhofer et al. | 514/277 |
| 3,816,434 | 6/1974 | Edenhofer et al. | 514/277 |
| 5,468,753 | 11/1995 | Coude et al. | 514/277 |
| 5,589,486 | 12/1996 | Harsangi et al. | 514/277 |

OTHER PUBLICATIONS

Derwent Publication Ltd. AN 82–88836E.
Journal of Medicinal Chemistry, vol. 15, No. 3, 1972 pp. 286–291.

*Primary Examiner*—James H. Reamer
*Attorney, Agent, or Firm*—George W. Johnston; Ellen Ciambrone Coletti; Robert A. Silverman

[57] ABSTRACT

A method of treating or preventing illnesses caused by a disorder of the dopamine system. The method comprises administering to a host requiring such treatment or prevention an effective amount of a pharmaceutical composition comprising a compound of the formula

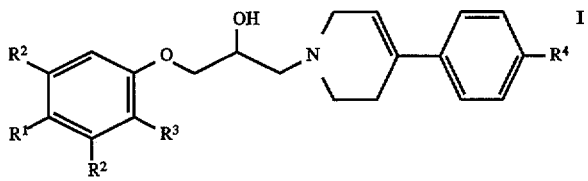

wherein $R^1$ is hydrogen, lower-alkyl, halogen, lower-alkoxy or nitro;

$R_2$ is hydrogen, lower alkyl or trifluoromethyl; and $R^3$ is hydrogen, lower alkyl, trifluoromethyl, benzyl, hydroxy-lower-alkyl, lower alkoxy, lower-alkyl-carbonyl-amino, carbonyl-lower-alkyl, benzyl, di-lower-alkyl-amino-carbonyl, carbonylamino or amino-carbonyl-amino; or $R^2$ and $R^3$ together optionally are a fused benzene ring and $R^4$ is hydrogen or halogen, or a pharmaceutically acceptable salt of a compound of formula I, and a pharmaceutically inert carrier material.

8 Claims, No Drawings

USE OF PHENOXY-PYRIDINE DERIVATIVES

SUMMARY OF THE INVENTION

The invention is concerned with a method of treating or preventing illnesses caused by a disorder of the dopamine system. The method comprises administering to a host requiring such treatment or prevention an effective amount of a pharmaceutical composition comprising a compound of the formula

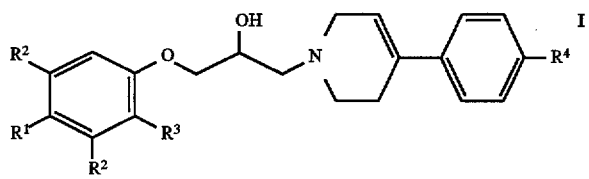

wherein $R^1$ is hydrogen, lower-alkyl, halogen, loweralkoxy or nitro;

$R^2$ is hydrogen, lower alkyl or trifluoromethyl; and $R^3$ is hydrogen, lower alkyl, trifluoromethyl, benzyl, hydroxy-lower-alkyl, lower alkoxy, lower-alkyl-carbonyl-amino, carbonyl-lower-alkyl, benzyl, di-lower-alkyl-amino-carbonyl, carbonylamino or amino-carbonyl-amino; or $R^2$ and $R^3$ together optionally are a fused benzene ring and $R^4$ is hydrogen or halogen, or a pharmaceutically acceptable salt of a compound of formula I, and a pharmaceutically inert carrier material.

DETAILED DESCRIPTION OF THE INVENTION

Compounds of formula I and salts thereof are known and described in U.S. Pat. No. 3,674,799. The compounds of formula I and salts thereof can be prepared by methods known and described in U.S. Pat. No. 3,674,799, incorporated herein by reference.

It has now surprisingly been found that the compounds of formula I and salts thereof are useful for treating and preventing illnesses which are caused by disorders of the dopamine system, for example, psychotic illnesses such as schizophrenia. The object of the present invention is accordingly the use of compounds of formula I and salts thereof for the treatment or prevention of psychotic illnesses which are caused by disorders of the dopamine system, in particular, the dopamine-$D_4$ receptor.

As used herein, the term "lower alkyl" denotes straight or branched chain lower alkyl of one to six carbon atoms, for example, methyl, ethyl, isopropyl, butyl, pentyl and the like. The term "lower alkoxy" denotes lower alkyl ether groups in which the lower alkyl is as described above, for example, methoxy, ethoxy, isopropoxy and the like. The term "halogen" denotes chlorine, bromine, fluorine and iodine. Of the halogen atoms, fluorine and chlorine are preferred.

The compounds of formula I and their salts have a high selective affinity to the dopamine-$D_4$ receptor. As a result use of the compounds of formula I or their salts results in significantly fewer side effects than would occur with the use of known neuroleptic agents, for example, haloperidol, which, as is known, bind to the $D_2$ or $D_3$ receptor. It has been found that in the case of schizophrenia the $D_2$ and $D_3$ receptor density increases by about 10%, while it can increase in the case of the $D_4$ receptor by about 600% (TIPS, July 1994, vol. 15, p. 264–70).

Compounds of formula I were characterized by their binding behavior at the $D_4$ receptor.

CHO cells (Chinese Hamster Ovary) were used in the test. Crude membranes were isolated by ultracentrifugation from $D_4$-CHO and $D_2$-CHO cells and were stored at −80° C. After thawing and homogenizing in a buffer solution (50 mM Tris, 1 mM EDTA, 5 mM KCl, 1.5 mM $CaCl_2$, 4 mM $MgCl_2$, pH 7.4) they were incubated at room temperature for 90 minutes with 200 pM [3H]-spiperone and an increasing concentration ($1\times10^{-11}$M to $1\times10^{-4}$M) of test compound. A non-specific binding was established by incubating in the presence of $1\times10^{-5}$M (+)-butaclamol. The unbound radioligand was removed by filtration through a GF/C glass filter and the bound radioactivity was determined by scintillation in a Packard TopCount. The following Table shows the binding behavior of compounds of formula I at the $D_4$ receptor.

The Ki value, a binding constant which shows the affinity of the compounds to the $D_4$ receptor, was determined by known methods using $^3$H-spiperone. The calculation of the value was effected with ligand.

TABLE 1

| Cpd. No. | $R^1$ | $R^2$ | $R^3$ | $R^4$ | Ki at $D_4$ [nM] |
|---|---|---|---|---|---|
| 1 | H | $CH_3$ | H | H | <100 |
| 2 | H | H | $CH_3$ | H | <100 |
| 3 | H | H | $CF_3$ | H | <100 |
| 4 | H | H | —$CH_2OH$ | H | <100 |
| 5 | H | H | —$OCH_3$ | H | <100 |
| 6 | H | H | —$NHCOCH_3$ | H | <100 |
| 7 | H | H | —$COCH_3$ | H | <100 |
| 8 | $CH_3$ | $CH_3$ | H | H | <100 |
| 9 | Cl | H | —$NHCOCH_3$ | H | <100 |
| 10 | H | $R^2$ and $R^3$ together benzene ring | | H | <100 |
| 11 | H | $CF_3$ | H | F | <100 |
| 12 | H | H | —$CONH_2$ | F | <100 |
| 13 | H | H | —$NHCONH_2$ | F | <100 |
| 14 | H | H | —$NHCOCH_3$ | Cl | <100 |

The compounds set forth in Table 1 are:

1. 1-(4-Phenyl-3,6-dihydro-2H-pyridin-1-yl)-3-m-tolyloxy-5-propan-2-ol
2. 1-(4-Phenyl-3,6-dihydro-2H-pyridin-1-yl)-3-o-tolyloxy-propan-2-ol
3. 1-(4-Phenyl-3,6-dihydro-2H-pyridin-1-yl)-3-(3-trifluoromethylphenoxy)-propan-2-ol
4. 1-(2-Hydroxymethyl-phenoxy)-3-(4-phenyl-3,6-dihydro-2H-pyridin-1-yl)-propan-2-ol
5. 1-(2-Methoxy-phenoxy)-3-(4-phenyl-3,6-dihydro-2H-pyridin-1-yl)-propan-2-ol
6. N-[2-[2-Hydroxy-3-(4-phenyl-3,6-dihydro-2H-pyridin-1-yl)-propoxy]-phenyl]-acetamide
7. 1-[2-[2-Hydroxy-3-(4-phenyl-3,6-dihydro-2H-pyridin-1-yl)-propoxy]-phenyl]-ethanone
8. 1-(3,4-Dimethyl-phenoxy)-3-(4-phenyl-3,6-dihydro-2H-pyridin-1-yl)-propan-2-ol
9. N-[5-Chloro-2-[2-hydroxy-3-(4-phenyl-3,6-dihydro-2H-pyridin-1-yl)-propoxy]-phenyl]acetamide
10. 1-(Naphthalen-1-yloxy)-3-(4-phenyl-3,6-dihydro-2H-pyridin-1-yl)-propan-2-ol
11. 1-[4-(4-Fluoro-phenyl)-3,6-dihydro-2H-pyridin-1-yl)-3-(3-trifluoromethyl-phenoxy)-propan-2-ol,
12. 2-[3-[4-(4-Fluoro-phenyl)-3,6-dihydro-2H-pyridinol-yl]-2-hydroxy-propoxy]-benzamide,
13. [2-[3-[4-(4-Fluoro-phenyl)-3,6-dihydro-2H-pyridin-1-yl]-2-hydroxy-propoxy]-phenyl]-urea 14 N-[2-[3-]4-(4-Chloro-phenyl)-3,6-dihydro-2H-pyridin-1yl]-2-hydroxy-propoxy]-phenyl]-acetamide.

The compounds of formula I and pharmaceutically acceptable salts thereof can be used as medicaments, for example, in the form of pharmaceutical preparations. The pharmaceutical preparations can be administered orally, for example, in the form of tablets, coated tablets, dragées, hard and soft gelatin capsules, solutions, emulsions or suspensions. The administration can, however, also be effected rectally, for example, in the form of suppositories, or parenterally, for example, in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like; depending on the nature of the active ingredient no carriers are, however, usually required in the case of soft gelatin capsules. Suitable carriers for the production of solutions and syrups are, for example, water, polyols, sucrose, invert sugar, glucose and the like. Adjuvants such as alcohols, polyols, glycerol, vegetable oils and the like can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances.

As mentioned earlier, medicaments containing a compound of formula I or a pharmaceutically acceptable salt thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical administration form together with one or more therapeutically inert carriers. The dosage can vary within wide limits and will, of course, be fitted to the individual requirements in each particular case. In general, a daily dosage of about 1 mg to 1000 mg should be appropriate.

EXAMPLE A

Tablets of the following composition are produced in the usual manner:

|  | mg/tablet |
|---|---|
| Active ingredient** | 100 |
| Powd. lactose | 95 |
| White corn starch | 35 |
| polyvinylpyrrolidone | 8 |
| Na carboxymethylstarch | 10 |
| Magnesium stearate | 2 |
| Tablet weight | 250 |

**Compound of formula I or a salt thereof.

EXAMPLE B

Tablets of the following composition are produced in the usual manner:

|  | mg/tablet |
|---|---|
| Active ingredient | 200 |
| Powd. lactose | 100 |
| White corn starch | 64 |
| polyvinylpyrrolidone | 12 |
| Na carboxymethylstarch | 20 |
| Magnesium stearate | 4 |
| Tablet weight | 400 |

EXAMPLE C

Capsules of the following composition are produced:

|  | mg/tablet |
|---|---|
| Active ingredient | 50 |
| Cryst. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatin capsules of suitable size.

We claim:

1. A method of treating or preventing an illness caused by a disorder of the dopamine system which comprises administering to a host in need of such treatment or prevention an effective amount of a pharmaceutical composition comprising a compound of the formula

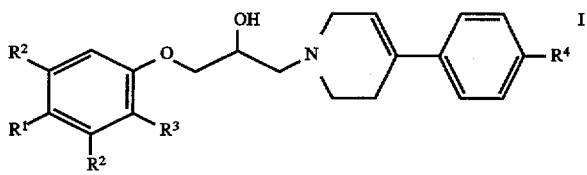

wherein $R^1$ is hydrogen, lower-alkyl, halogen, lower-alkoxy or nitro;

$R^2$ is hydrogen, lower alkyl or trifluoromethyl; and $R^3$ is hydrogen, lower alkyl, trifluoromethyl, benzyl, hydroxy-lower-alkyl, lower alkoxy, lower-alkyl-carbonyl-amino, carbonyl-lower-alkyl, benzyl, di-lower-alkyl-amino-carbonyl, carbonyl-amino or amino-carbonyl-amino; or $R^2$ and $R^3$ together optionally are a fused benzene ring and $R^4$ is hydrogen or halogen, or a pharmaceutically acceptable salt of a compound of formula I, and a pharmaceutically inert carrier material.

2. The method of claim 1, wherein $R^1$ is hydrogen, $R^2$ is hydrogen or trifluoromethyl, $R^3$ is hydrogen, carbonyl-amino or acetyl-amino and $R^4$ is fluorine or chlorine.

3. The method of claim 1, wherein the compound of formula I is 1-[4-(4-fluoro-phenyl)-3,6-dihydro-2H-pyridin-1-yl]-3-(3-trifluoromethyl-phenoxy)-propan-2-ol.

4. The methods of claim 1, wherein the compound of formula 1 is N-[2-[3-[4-(4-chloro-phenyl)-3,6-dihydro-2H-pyridin-1-yl]-2-hydroxy-propoxy]phenyl]-acetamide.

5. The method of claim 1, wherein the compound of formula I is 2-[3-[4-(4-fluoro-phenyl)-3,6-dihydro-2H-pyridin-1-yl]-2-hydroxy-propoxy]-benzamide.

6. The method of claim 1, wherein the illness is a psychotic illness.

7. The method of claim 6, wherein the psychotic illness is schizophrenia.

8. The method of claim 1, wherein the effective amount is 1 mg to 1000 mg per day.

* * * * *